United States Patent [19]
Baker et al.

[11] Patent Number: 4,768,390
[45] Date of Patent: Sep. 6, 1988

[54] INSTRUMENT FOR MEASURING THE PHOTOSYNTHETIC ACTIVITIES OF PLANTS

[75] Inventors: Neil R. Baker, Brightlingsea; Stephen P. Long, Wivenhoe, both of England

[73] Assignee: The British Petroleum Company p.l.c., London, England

[21] Appl. No.: 9,342

[22] PCT Filed: Jun. 12, 1986

[86] PCT No.: PCT/GB86/00341
§ 371 Date: Feb. 3, 1987
§ 102(e) Date: Feb. 3, 1987

[87] PCT Pub. No.: WO86/07461
PCT Pub. Date: Dec. 18, 1986

[30] Foreign Application Priority Data
Jun. 14, 1985 [GB] United Kingdom ................. 8515132

[51] Int. Cl.⁴ ..................... G01N 33/48; G01N 21/64
[52] U.S. Cl. ..................................... 73/865.6; 73/336; 356/432; 374/142
[58] Field of Search ................... 73/865.6, 866, 23, 29, 73/73, 76, 336; 374/142; 250/304, 340, 341, 349; 356/432

[56] References Cited

U.S. PATENT DOCUMENTS

| | | | |
|---|---|---|---|
| 3,473,022 | 10/1969 | Walz et al. | 250/349 X |
| 3,613,308 | 10/1971 | Klein et al. | 47/17 |
| 3,871,888 | 3/1975 | Michel-Wolwertz et al. | 524/9 X |
| 3,904,395 | 9/1975 | Eilrich et al. | 71/92 |
| 4,066,435 | 1/1978 | Howe | 71/86 |
| 4,472,194 | 9/1984 | Van Assche et al. | 71/121 |
| 4,533,252 | 8/1985 | Cahen et al. | 356/440 X |
| 4,665,059 | 5/1987 | Tozawa et al. | 71/88 X |
| 4,678,330 | 7/1987 | Gutschick et al. | 356/432 X |

FOREIGN PATENT DOCUMENTS
3303510 7/1983 Fed. Rep. of Germany .
1590544 5/1970 France .

OTHER PUBLICATIONS
"The Relationship Between Carbon Dioxide Fixation and Chlorophyll a Fluorescence During Induction of Photosynthesis in Maize Leaves at Different Temperatures and Carbon Dioxide Concentrations"; *Planta*, vol. 160, pp. 550–558; 1984; C. R. Ireland et al.
"Chlorophyll a Fluorescence: Can It Shed Light on Fundamental Questions in Photosynthetic Carbon Dioxide Fixation?"; *Plant, Cell and Environment;* vol. 8, pp. 439–448; 1985; Mirta N. Sivak et al.

*Primary Examiner*—Tom Noland
*Attorney, Agent, or Firm*—Morgan & Finnegan

[57] ABSTRACT

An instrument (2) for simultaneously measuring a plurality of parameters indicative of photosynthetic activity of a leaf in vivo comprises:
(a) a gas tight chamber (4) for enclosing the leaf (5),
(b) light emitting diode means (10) for illuminating the leaf within the chamber with modulated light not capable of driving photosynthesis,
(c) photodiode detector means (14) for detecting modulated fluorescence emission from the leaf,
(d) wide perspex core means for illuminating the leaf with photosynthetically active light,
(e) quantor sensor means (43) for measuring the light absorbed by the leaf,
(f) and infra red gas analyzer means (32) for measuring the rate of uptake of carbon dioxide gas by the leaf.

The instrument may also comprise means for measuring the rate of loss of water by the leaf, and for measuring the temperature in the chamber.

The invention includes a method of simultaneously measuring a plurality of parameters indicative of photosynthetic activity of a leaf in vivo.

14 Claims, 2 Drawing Sheets

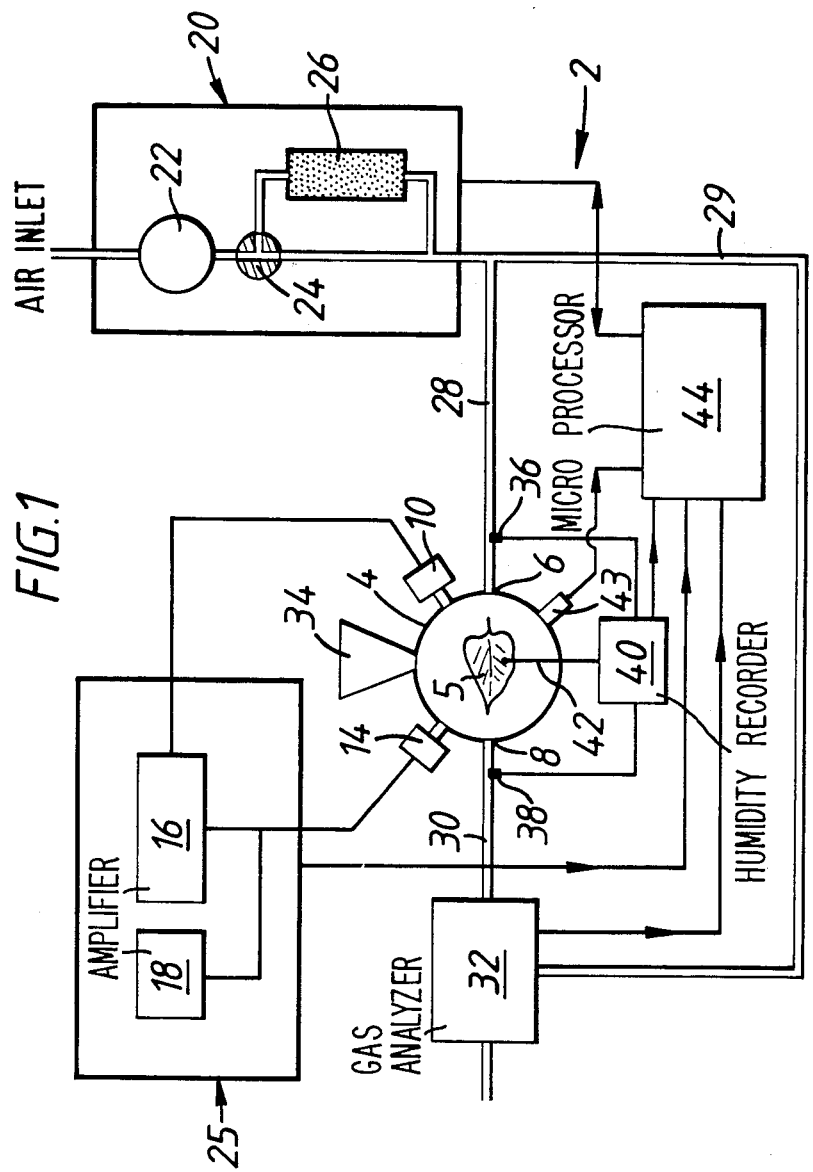

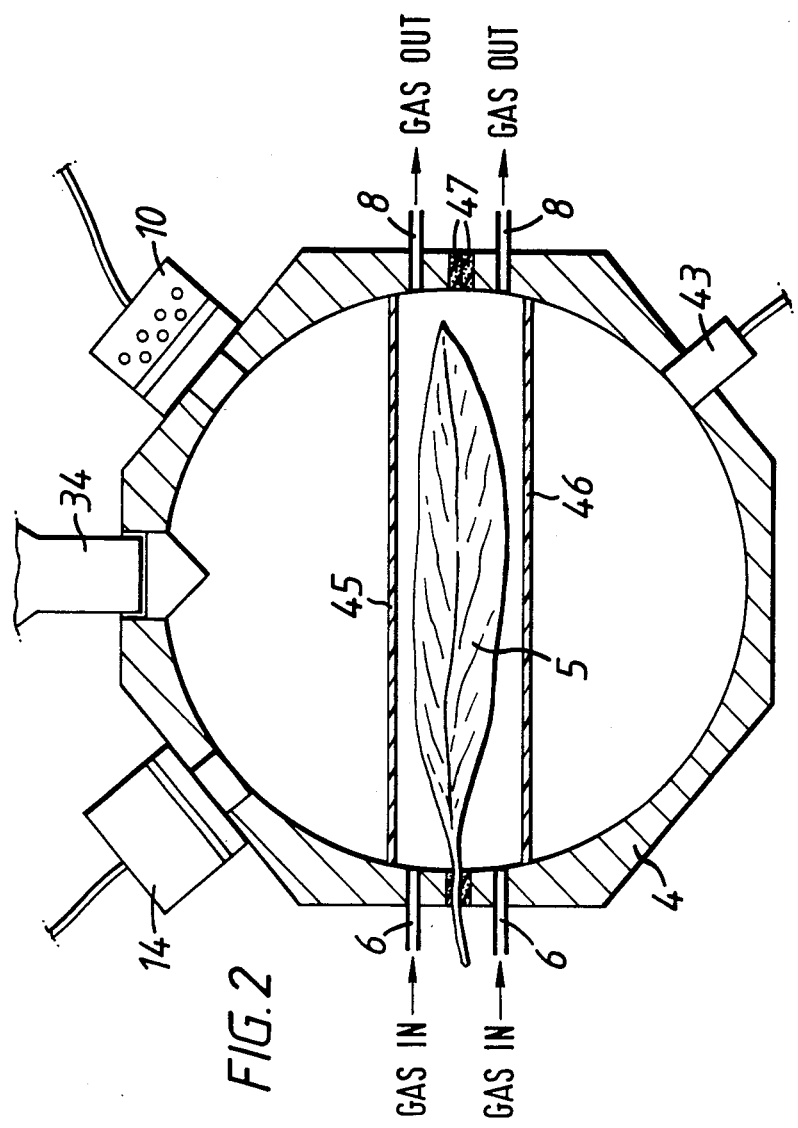

INSTRUMENT FOR MEASURING THE PHOTOSYNTHETIC ACTIVITIES OF PLANTS

BACKGROUND OF INVENTION

1. Field of Invention

The present invention is concerned with an instrument for measuring the photosynthetic activities and capacities of plants. More particularly it is concerned with an instrument for measuring simultaneous chlorophyll fluorescence emission, $CO_2$ assimilation rate and, if desired, transpiration rate, parameters which are all characteristics of a plant's general metabolic and health status.

Recent demonstrations that changes in chlorophyll fluorescence emission during the induction of photosynthesis are closely related to the rate of carbon dioxide assimilation have increased the interest in the application of fluorescence as a convenient monitor of leaf photosynthetic activity.

2. Description of Prior Art

Apparatus and techniques for measuring chlorophyll fluorescence emission from leaves in the laboratory are known. Chlorophyll fluorescence emission is indicative of the light reactions of photosynthesis, and is the first detectable parameter to indicate a change in photosynthetic activity. It has been found that the level of photosynthetic activity of the leaf as evidenced by the fluorescence emission can provide not only evidence of the general health of the leaf but also how the leaf responds to changes in its environment. The response may be rapid and provide an indication of the leaf's activity well in advance of any visible physical change in the leaf.

Simultaneous measurements of $CO_2$ assimilation rate of a leaf and continuous fluorescence signals have previously been made under laboratory conditions. To date, apparatus for measuring $CO_2$ assimilation rate and the fluorescence signals have employed the continuous means of using white light fitted with a red-removing filter, so that continuous fluorescence induction curves may be generated by the red-deficient light, and by detecting the fluorescence of the leaf, which is emitted as red light, with a continuous detector fitted with suitable filters so that only red light, all of which is derived from fluorescence of the leaf is detected. This method of detecting fluorescence gives a measure of the fluorescence induced when light deficient in the red portion of the spectrum is incident upon the leaf.

In field conditions white light contains red light ie the part of the spectrum which would be eliminated by the red removing filter. Some of the light, which would not be present in the red-deficient light is capable of driving photosynthesis. The continuous method described above is not representative of the activity of the plant when white light is incident upon it, as under field conditions. Therefore, it was desirable to develop a system for measuring the fluorescence response of a leaf which is exposed to white light, simultaneously with the measurement of $CO_2$ assimilation by the leaf.

SUMMARY OF THE INVENTION

An instrument has now been devised which can be used to simultaneously measure $CO_2$ assimilation and parameters of chlorophyll fluorescence by the leaf induced by white light eg sunlight or artificial white light.

According to the present invention an instrument (2) for simultaneously measuring a plurality of parameters indicative of photosynthetic activity of a leaf (5) in vivo comprises (a) a gas tight chamber (4) for the leaf (5), (b) means (10) for illuminating the leaf with modulated light of insufficient intensity to drive photosynthesis, (c) means (14) for detecting modulated fluoroescence emission from the leaf, (d) means for illuminating the leaf with photosynthetically active light, (e) means (43) for measuring the light absorbed by the leaf, (f) and means (32) for measuring the rate of uptake of carbon dioxide gas of the leaf.

The term leaf in the present specification includes a part of a leaf and also more than one leaf. The term leaf also refers to any part of a plant capable of photosynthesis.

Plant photosynthetic activity can be measued directly by assessing $CO_2$ uptake. Infra-red spectroscopy provides a rapid non-destructive means of assessing $CO_2$ uptake. By combining this with simultaneous measurements of light levels when the leaf is exposed to white light and ambient $CO_2$, the leaf's light and carboxylation efficiencies, respectively, can be determined. The instrument allows the simultaneous measurement of all of the above parameters on the same leaf tissue.

Preferably, the instrument also comprises a means for measuring the rate of loss of water by the leaf for example means for measuring the water content in the inlet line and outlet line to the chamber. Thus, by combining transpiration rate measurements with simultaneous measurements of the $CO_2$ fixation rate, the leaf's water-use efficiency can also be determined. This is the ratio of water loss to carbon gain by the leaf.

It is preferable that the instrument comprises a means for measuring the temperature in the chamber.

It is desirable that measurements made in the chamber holding the leaf are subject to minimal errors.

The chamber enclosing the leaf may be formed in two parts, which may be hinged if desired, so that it can be placed around and removed from the leaf.

The edges of the chamber parts which come together to form the enclosed chamber are preferably made of resilient material (eg foam rubber) to avoid damage to the plant. The parts may be held by catches or clamps to hold the chamber firmly on the plant. These resilient edges may also form the gas tight seal of the chamber.

The chamber should be substantially opaque to light, so that light admitted to the chamber cannot escape.

The chamber parts may be made of metal, preferably a light alloy, conveniently closed with means for piping light to the interior thereof.

Preferably, the chamber has curved surfaces, and most preferably it is spherical. It is also preferred that the internal surface of the chamber is coated with a high reflectance coating, e.g. a white high reflectance paint or a coating obtained by burning magnesium onto the surface. These optional features are preferred since they reduce the absorbance of light by the chamber.

With the above features, the only significant effective dissipation of light in the chamber is by an enclosed absorbing body, eg the leaf.

Since leaves come in a wide variety of shapes and sizes the instrument may have a number of interchangeable chambers varying in shape and size, designed to suit particular types of plant. With this embodiment the instrument may have a frame for the various light and gas inlet and outlet connections to the chamber and means for holding the interchangeable chambers so that their inlets and outlets are aligned with the matching connections.

The frequency of the incident modulated light is selected so that it is different from the frequency of the emitted fluorescence eg it is weak, yellow modulated light so that all the light detected at the emitted frequency is caused by fluorescence.

The modulated light source may be one or more suitably pulsed light emitting diodes. A suitable system for this light production may comprise a master oscillator, a diode array and one or more high precision, visible short pass filters. It is desirable that the modulated light should generate minimal variable fluorescence of itself, so that such additional variable fluorescence produced on exposure to other radiation sources is indicative of the leaf's photosynthetic activities.

The modulated light may be monochromatic or polychromatic, but is preferably monochromatic.

The modulated light may be projected onto the top or the underside of a leaf and the light may be projected in any convenient way. Thus, the modulated light may be projected directly onto the leaf in the chamber. The light source may be at a distance from the chamber with the light being transmitted from the source to the chamber by eg a fibre optic cable.

The modulated fluorescence emission detector may be one or more photodiodes. The output signal may be amplified in one or more stages and recorded on eg a chart recorder. The detector may be protected by an interference filter of suitable wavelength and band width so that it detects only light of the wavelengths corresponding to the wavelengths of chlorophyll fluorescence, and between the amplifiers and the recorder the output signal may be rectified and buffered.

The amplifier or amplifiers may be linked to the master oscillator to ensure they operate at the same frequency as that generated by the master oscillator.

Thus the modulated fluorescence detector is locked in to the frequency of the modulation of the modulated light and consequently only monitors chlorophyll fluorescence generated by the modulated light.

The amount of fluorescence generated by light incident upon the leaf is indicative of the photosynthetic capability of the leaf. When only the modulated light is incident upon the leaf. Since the modulated light cannot drive photosynthesis the proportion of the modulated light which causes fluorescence is constant over time, ie the background level.

When the photosynthically active light starts to be incident upon the leaf in addition to the modulated light, the leaf's photosynthetic apparatus begins to operate, and consequently there is a transient increase in the proportion of the total incident light absorbed by the leaf which is emitted as fluorescence. The proportion of modulated light which is converted to fluorescence by the leaf also alters transiently in a similar manner. The parameters of the peak in fluorescence caused by the yellow modulated light when photosynthesis commences are indicative of the photosynthetic activity of the plant.

Thus the modulated fluorescence detector is locked in to the frequency of the modulation of the modulated light and consequently only monitors chlorophyll fluorescence generated by the modulated light.

A fluorescence detector system using a modulated light source as indicated above is capable of operation in normal light conditions. Hence the instrument can be used in the open air in any light conditions or in greenhouses or other covered areas of cultivation, including, if necessary, areas which are artificially illuminated.

The means for illuminating the leaf with light capable of driving photosynthesis may be a wide perspex cone used to trap white light (e.g. sunlight) which may enter the chamber. Preferably the instrument may also have a source of white light which can be projected onto the plant portion in addition to the modulated light and any natural light. There are preferably means, e.g. iris diaphragm of filters, for varying the intensity and quality of this white light.

The white light source may be fitted with a removable red removing filter to allow continuous fluorescence induction curves to be generated by red-deficient light, thereby allowing additional information to be obtained using the instrument.

The fluorescence generated by the red-deficient light can be picked up by the same detector as that used for the modulated light. A separate detector is not required. The red-deficient light can be projected onto the leaf in a manner similar to that for the modulated light, either directly or via a fibre optic cable.

In addition to the fluorescence detection system described above, the instrument has, as previously explained, a system for measuring $CO_2$ assimilation and, preferably, a separate system for measuring transpiration.

The system for measuring the $CO_2$ assimilation rate of the enclosed leaf comprises an inlet to and an outlet from the chamber, a pump or pumps for passing gas through the chamber, a gas analyser for measuring the $CO_2$ content of gas leaving the chamber and preferably means for controlling the $CO_2$ content of gas entering the chamber. A reference flow passes gas from prior to the inlet to the gas analyser.

The chamber has means for monitoring the photosynthetically active radiation within the chamber, that is, light capable of driving photosynthesis. This may be in the form of a quantum sensor fitted with filters. This, combined with the temperature and humidity probes, monitors the overall microclimate within the chamber. Such measurement is necessary for determination of the plant's quantum efficiency and for correct interpretation of the recorded data.

The instrument may be operated manually but is preferably controlled by a microprocessor with suitable programs for actuation and control, data acquisition and storage, and data analysis. The data may be presented as unit-corrected read outs of $CO_2$ fixation rate, chlorophyll fluorescence emission parameters, transpiration rate, quantum efficiency and the leaf internal carbon dioxide concentration. The instrument may be powered by rechargeable batteries.

BRIEF DESCRIPTION OF THE DRAWINGS

The invention is illustrated by reference to the accompanying drawings in which

FIG. 1 is a block diagram of the instrument for measurement of photosynthesis performance and FIG. 2 is an enlarged cross section of the spherical leaf chamber taken on a plane containing a diameter.

DESCRIPTION OF PREFERRED EMBODIMENTS

Referring to FIG. 1 the instrument indicated generally by reference numeral 2 comprises a spherical gas tight chamber 4 for holding a leaf 5. The chamber 4 is provided with an inlet 6, an outlet 8 and a source of modulated light in the form of a light emitting diode 10 for illuminating the leaf 5. Means for detecting and measuring modulated fluorescence emission from the leaf is provided in the form of a photodiode detector 14 operatively connected to a modulated amplifier 16. The detector 14 is locked in to the same frequency as the light emitting diode 10 to permit measurement of fluorescence under daylight conditions. The photodiodes detector is also operatively connected to a simple amplifier 18 allowing continuous fluorescence to be measured when the leaf 5 is illuminated by a source of red-deficient light.

The instrument includes a gas control system indicated generally by reference numeral 20 which comprises a pump 22, flow controller 24 and carbon dioxide adsorber 26. The gas control system 20 is connected by line 28 to the inlet 6 of the chamber 4. Line 29 provides a reference flow connecting line 28 to an infra-red gas analyser 32. The outlet 8 of the chamber 4 is connected by line 30 to the infra red gas analyser 32 capable of measuring both the absolute concentration of carbon dioxide and the difference in concentration between a measured flow and the reference flow and hence the rate of uptake of carbon dioxide by the leaf.

The chamber 4 is further provided with a source of continuous white light 34 or alternatively a perspex come to collect sunlight. Electronic humidity probes 36 and 38 are provided in lines 28 and 30 respectively to measure the humidity difference in the gas flow across the chamber 4 and hence the rate of loss of water by the leaf ie the leaf transpiration rate. Signals from the probes 36 and 38 are passed to a humidity difference recorder 40 which also receives signals from a thermocouple probe 42 which measures the temperature of the leaf 5. A microprocessor 44 is provided which receives data from the gas analyser 32, the humidity recorder 40, the fluorescence measuring system 25, the quantum sensor 43 and the gas control system 20.

Referring to FIG. 2 the chamber 4 is shown holding the leaf 5. The chamber has soft foam rubber seals 47 for making an air tight seal against the stem of the leaf 5. The chamber 4 has inlets 6 arranged to pass the gas over and below the surfaces of the leaf and outlets 8 from which the air is withdrawn from the chamber. The chamber is provided with upper and lower clear perspex plates 45 and 46 arranged to reduce the volume of the gas exchange zone and increase the response time for measurement of gas exchange kinetics. The internal surface of the chamber is of spherical form and coated with a white high reflectance paint (which reflects over 99% of the incident light). The chamber thus acts as a light integrating sphere.

Theoretically, if there is 100% internal reflectance, the only dissipation of light within the sphere is by absorption by an enclosed absorbing body. Therefore, the difference in light flux in the chamber with and without an enclosed leaf is equal to the amount of light directly absorbed by the leaf. In order to minimise the amount of absorption that does occur at the chamber walls a spherical chamber is employed which minimises the number of internal reflections. Further, by using a black body of known absorptivity, the actual absorptivity of the chamber can be quantified. This parameter is then employed during the subsequent calculation of leaf absorptivity correct for the light absorption by the chamber when the various probes are in position. Having determined leaf absorptivity, the absolute quantum efficiency of $CO_2$ assimilation by the leaf can be determined, i.e. the amount of $CO_2$ assimilated by the leaf per photon absorbed by the leaf.

In operation an attached leaf is enclosed in the chamber 4 and a gas tight seal made against the stem of the leaf by means of the soft foam rubber seal 47. Air is passed from the gas control system 20 through the chamber 4. The flow rate of the air is precisely controlled and the concentration of carbon dioxide in the air is adjusted as required by passing varying proportions of the air flow through the carbon dioxide absorbing column 26. The inlets 6 to the chamber 4 are made small compared to the size of the chamber thereby causing turbulent flow to aid mixing of the gases. After passing over the leaf 5 the gas passes through outlets 8 and line 30 to the gas analyser 32 which measures both the absolute concentration of carbon dioxide and the difference in concentration between the analysis flow and a reference flow. From these measurements the rate of uptake of carbon dioxide by the leaf can be determined.

The leaf 5 is illuminated by modulated light from the light emitting diode 10 and the modulated fluorescence emission measured by the photodiode detector 14. The high intensity white light source 34 is operated as a removable device to enable fluorescence induction curves to be measured in the field and to examine the effects of the changing light intensity on photosynthesis.

The amount of light adsorbed by the leaf is determined by operating the light sources and detectors with no leaf in the chamber.

The humidity and temperature are measured by the electronic humidity probes 36 and 38 and thermocouple probe 42 respectively, from which the humidity difference in the gas flow across the chamber and hence the leaf transpiration rate can be determined. The quantum sensor 43 measures the photosynthetic active radiation. Analogue output signals from the recorders are sent to the microprocessor 44 for rapid data acquisition and analysis.

The arrows indicate the direction of the flow of information.

The instrument described above is, (i) capable of carrying out the measurements on a leaf without damaging the leaf and whilst the leaf is still attached to the rest of the plant, (ii) capable of measuring photosynthesis parameters in normal light conditions which may vary from shade to strong direct sunlight, (iii) capable of being operated by a portable power source such as a rechargeable battery and (iv) compact and portable.

We claim:

1. An instrument for simultaneously measuring a plurality of parameters indicative of photosynthetic activity of a leaf in vivo, said instrument comprising
   (a) a gas tight chamber for enclosing the leaf,
   (b) means for illuminating the leaf within the chamber with modulated light not capable of driving photosynthesis,
   (c) means for detecting modulated fluorescence emission from the leaf,
   (d) means for illuminating the leaf with photosynthetically active radiation,
   (e) means for measuring the light absorbed by the leaf,
   (f) and means for measuring the rate of uptake of carbon dioxide gas by the leaf.

2. An instrument according to claim 1 having means for measuring the rate of loss of water by the leaf.

3. An instrument as claimed in claim 2 wherein the means for measuring the rate of loss of water by the leaf comprises humidity detectors located to measure the water content of the gas supplied to and withdrawn from the chamber.

4. An instrument according to claim 1 having means for measuring the temperature in the chamber.

5. An instrument as claimed in claim 1 wherein the means for measuring the rate of uptake of carbon dioxide gas comprises means for supplying and controlling the flow of a carbon dioxide-containing gas stream to the chamber and means for withdrawing the gas from the chamber and means for measuring the carbon dioxide content of the gas supplied to and withdrawn from the chamber.

6. An instrument as claimed in claim 5 wherein a means is provided for controllably varying the carbon dioxide content of the gas supplied to the chamber.

7. An instrument as claimed in claim 1 characterised in that the means for detecting modulated fluorescence emission comprises a photodiode detector capable of being locked into the same frequency as the modulated light source.

8. An instrument as claimed in claim 7 wherein the photodiode detector is operatively connected to a modulated amplifier.

9. An instrument as claimed in claim 1 wherein the chamber (4) has an internal curved surface.

10. An instrument according to claim 1 wherein the modulated light is monochromatic.

11. A method for simultaneously measuring a plurality of parameters indicative of photosynthetic activity of a leaf which method comprises
illuminating the leaf with modulated light not capable of driving photosynthesis and measuring the modulated fluorescence emission from the leaf, illuminating the leaf with light capable of driving photosynthesis and measuring the light absorbed by the leaf and measuring the rate of uptake of carbon dioxide gas by the leaf.

12. A method as claimed in claim 11 which includes measuring the rate of uptake of water by the leaf.

13. A method as claimed in claim 11 which includes measuring the temperature of the leaf.

14. A method as claimed in claim 11 wherein the leaf is enclosed in a chamber whose internal surfaces have a high light reflectance so that substantially all the light adsorbed is adsorbed by the leaf.

* * * * *